United States Patent [19]

Zambias et al.

[11] Patent Number: 5,006,549
[45] Date of Patent: Apr. 9, 1991

[54] 7-AROYL-4-HYDROXY-3-METHYL-BENZOFURANS AS DUAL INHIBITORS OF CYCLOOXYGENASE AND 5-LIPOXYGENASE

[75] Inventors: Robert A. Zambias, Springfield; Milton L. Hammond, Somerville, both of N.J.

[73] Assignee: Merck & Co., Inc., Rahway, N.J.

[21] Appl. No.: 356,151

[22] Filed: May 24, 1989

[51] Int. Cl.$^5$ .................. A61K 31/38; A61K 31/44; C07D 409/00; C07D 305/12
[52] U.S. Cl. .................. 514/444; 514/337; 514/422; 514/469; 546/269; 548/525; 549/320; 549/471; 549/60
[58] Field of Search .................. 549/60, 471, 320; 548/525; 546/269; 514/337, 422, 469, 444

[56] References Cited

U.S. PATENT DOCUMENTS

| | | |
|---|---|---|
| 4,172,082 | 10/1979 | Moore . |
| 4,431,656 | 2/1984 | Katsumi et al. . |
| 4,548,948 | 10/1985 | Ward et al. .................. 549/60 |
| 4,743,606 | 5/1988 | Lazer . |
| 4,775,679 | 10/1988 | Chang et al. .................. 549/60 |
| 4,816,473 | 3/1989 | Dunn .................. 549/60 |

FOREIGN PATENT DOCUMENTS 2600065 12/1987 France .................. 549/60

OTHER PUBLICATIONS

Annual Reports in Medicinal Chemistry, vol. 22, Chapter 20, p. 205, (1987).
Annual Reports in Medicinal Chemistry, vol. 23, Section 4, pp. 184–189 (1989).
Katsumi, Ikuo et al., Studies on Styrene Derivatives II Synthesis and Anti-inflammatory Activity of 3,5-Di--tert-butyl-4-hydroxystyrenes, Chem. Pharm. Bull., vol. 34, pp. 1619–1627 (1986).
Lazer, E.S. et al., Antiinflammatory 2,6-Di-ter-t-butyl-4-(2-arylethenyl) phenyls, J. Med. Chem., vol. 32, pp. 100–104 (1989).

Primary Examiner—Alan Siegel
Attorney, Agent, or Firm—Curtis C. Panzer; Hesna J. Pfeiffer

[57] ABSTRACT

Novel 7-Aroyl-4-Hydroxy-3-Methyl-Benzofurans of the following general formula (I) are disclosed:

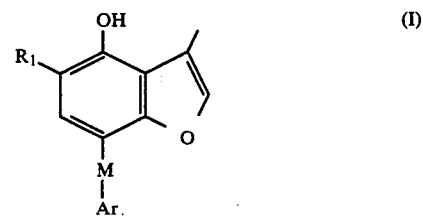

The compounds are found to be potent dual inhibitors of cyclooxygenase and 5-lipoxygenase.

8 Claims, No Drawings

7-AROYL-4-HYDROXY-3-METHYL-BENZOFURANS AS DUAL INHIBITORS OF CYCLOOXYGENASE AND 5-LIPOXYGENASE

BACKGROUND OF THE INVENTION

Since the development of the first nonsteroidal antiinflammatory agents (NSAIDs) in the early 1960's, much work has been done to elucidate the mode of action of these compounds in vivo. It is currently believed that these materials exert their therapeutic effects by inhibiting the action of the cyclooxygenase enzyme on arachidonic acid, thus blocking the formation of the prostaglandins (PG's), potent mediators of inflammation.

More recently it has been discovered that the enzyme 5-lipoxygenase catalyzes the first two steps in the formation of a series of biologically important metabolites of arachidonic acid, the leukotrienes. These metabolites were found to be potent regulators of vascular permeability, one of the classic signs of inflammation. In addition, leukotriene B$_4$ (LTB$_4$) has been shown to be a powerful chemotaxin for phagocytic cells while LTC$_4$ and LTD$_4$ were identified as the slow reacting substance of anaphylaxis. It therefore seems reasonable that a potent inhibitor of cyclooxygenase and 5-lipoxygenase, a dual inhibitor, should provide advantages over inhibitiors of cyclooxygenase alone, and many agents of this type are currently under investigation. See Samuelson, B. Science 1983, 220, 568; Venuti, M. C.; Annual Reports in Medicinal Chemistry 1987, 22, 205 and references cited therein.

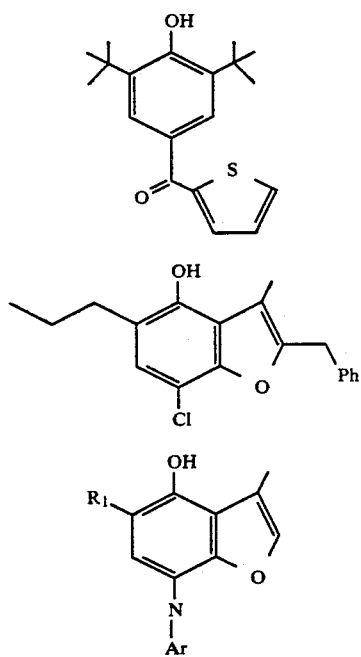

Recently, 2,6-di-tert-butyl-4-(2-thienoyl) phenol, compound A, was demonstrated to be a novel antiinflammatory agent in several animal models of inflammation. See Moore, G. G. I.; Swingle, K. F. Agents and Actions 1982, 12, 5. Interestingly, A inhibited both the prostaglandin and leukotriene pathways of the arachidonic acid cascade in vitro, although not to an equal extent. In particular, A had an IC$_{50}$ of 0.5 mM against cyclooxygenase in a bovine seminal vesicle microsomal enzyme preparation but was fortyfold less potent at inhibiting guinea pig lung 5-lipoxygenase with an IC$_{50}$ of 20 mM.

E. S. Lazer et. al., describes analogs of A wherein the thienoyl moeity is replaced by certain 4-arylethenyl groups. See J. Med. Chem. (1989), 32, 100–104. 4-lactonylexomethenyl and 4-(N-methoxypyrrolidinoyl) substituents have also been described. See Ann. Rept. Med. Chem. (1987) Vol 22, 205; Ann. Rept. Med. Chem. (1988) Vol. 23, p. 184. These references, however, do not disclose the novel compounds of the present invention nor do they disclose the relatively equal potency of such compounds against both cyclooxygenase and lipoxygenase.

A 4-benzofuranol, Compound B, has been reported to be a potent and selective inhibitor of LTB$_4$ biosynthesis in intact rat PMN (IC$_{50}$=0.24 mM). See Belanger, P.; Maycock, A.; Guindon, T.; Bach, T.; Dollob, A. L.; Dufrense, C.; Ford-Hutchinson, A. W.; Gale, P. H.; Hopple, S.; Lau, C. K.; Letts, L. G.; Luell, S.; McFarlane, C. S.; Macintyre, E.; Meurer, R.; Miller, D. K.; Piechuta, H.; Riendeau, D.; Rokach, J.; Rouzer, C.; Scheigetz, J. Canandian Journal of Physiology and Pharmacology 1987, 65, 2441. The selectivity of L-656,224 was shown through its relative lack of activity on cyclooxygenase being a hundred times less potent in the RSV CO assay (IC$_{50}$=25 mM).

DETAILED DESCRIPTION OF THE INVENTION

This invention relates to novel compounds of formula I

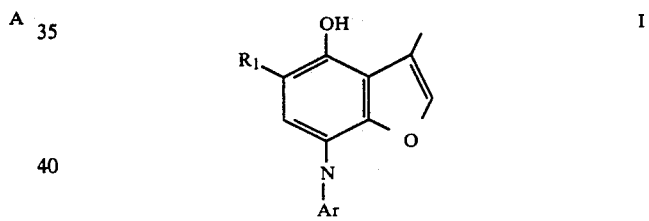

or pharmaceutically acceptable salts thereof wherein:
R$_1$ is selected from the group consisting of:
 (a) hydrogen,
 (b) C$_{1-6}$alkyl, and
 (c) C$_{3-6}$alkenyl;
M is selected from the group consisting of:
 (a) a carbon-carbon bond,
 (b) —C(H)=,
 (c) —C(H)=C(H)—,
 (d) —CH$_2$C(H)=C(H)—, and
 (e) —C(O)—;
Ar is selected from the group consisting of:
 (a) thienyl,
 (b) halothienyl,
 (c) phenyl,
 (d) halophenyl,
 (e) benzyl,
 (f) halobenzyl,
 (g) n-methoxypyrrolidinoyl,
 (h) γ-lactonyl, and
 (i) pyridyl.

A class within the scope of the invention is the class of compounds wherein:
M is
 (a) a carbon-carbon bond, (b) —C(H)=C(H)—, or
(c) —C(O)—; and Ar is
(a) thienyl,
(b) halothienyl,
(c) phenyl, and
(d) halophenyl.

A subclass within the scope of the invention is the compounds wherein:

$R_1$ is
(a) hydrogen,
(b) methyl,
(c) n-propyl, or
(d) tert-butyl; and

Ar is
(a) thienyl,
(b) chlorothienyl,
(c) phenyl, or
(d) chlorophenyl.

Species within the scope of the invention are:
(1) 7-(2-thienoyl)-4-hydroxy-3-methylbenzofuran,
(2) 7-benzoyl-4-hydroxy-3-methylbenzofuran,
(3) 7-(2-thienoyl)-5-allyl-4-hydroxy-3-methyl-benzofuran,
(4) 7-(2-thienoyl)-5-(n-propyl)-4-hydroxy-3-methylbenzofuran,
(5) 7-(2-thienoyl)-5-tert-butyl-4-hydroxy-3-methylbenzofuran,
(6) 7-benzoyl-5-tert-butyl-4-hydroxy-3-methyl-benzofuran,
(7) 7-(p-Cl-benzoyl)-5-tert-butyl-4-hydroxy-3-methylbenzofuran,
and pharmaceutically acceptable salts thereof.

The compounds of the present invention are conveniently prepared using the procedures described generally below and more explicitly in the Examples section thereafter.

Scheme 1

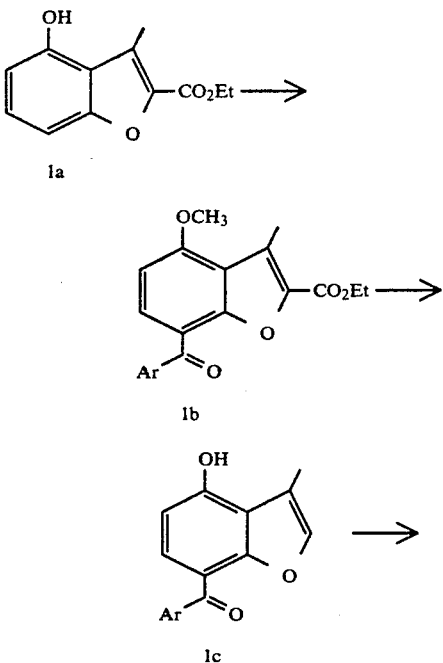

-continued
Scheme 1

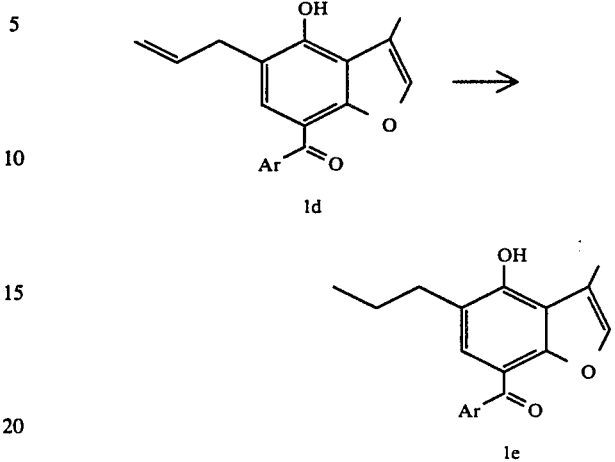

The synthesis of compounds of formula I are shown in Schemes 1 to 4.

Access to the 7-aroyls with linear alkyls at position 5 is shown in Scheme 1. Methylation of 1a, followed by Friedel Crafts acylation (such as with $AlCl_3$, $CH_2Cl_2$), provided the ketones (1b) in excellent yield. Royer, R.; Lamotte, G.; Demerseman, P. Eur. J. Med. Chem.-Chemica Therapeutica 1974, 9, 136. Belanger, P. C.; Dufrense, C.; Lau, C. K.; Scheigetz, J. Organic Procedures and Procedings International Briefs 1988, 20, 299. Saponification of 1b gave the corresponding carboxylic acid which was then decarboxylated and demethylated to 1c. Benzofuranol 1c was alkylated with allyl bromide and potassium carbonate. The resulting allyl ether underwent thermal Claisen rearrangement in refluxing 1,3-dichlorobenzene to give 1d. Simple hydrogenation over palladium on carbon in ethanol gave 1e.

SCHEME 2

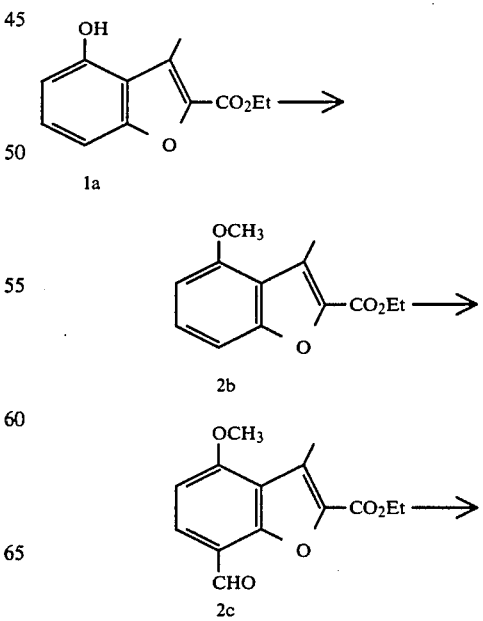

-continued
SCHEME 2

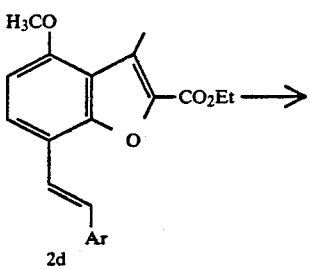
2d

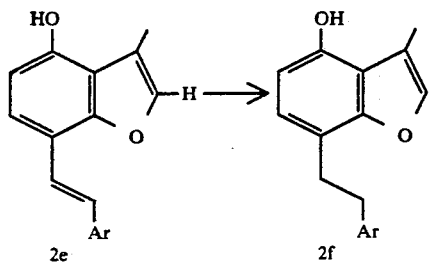
2e  2f

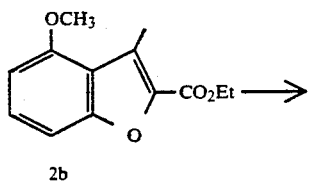
2b

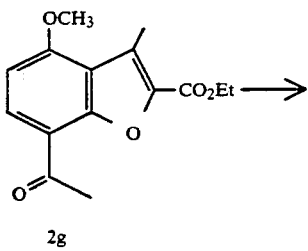
2g

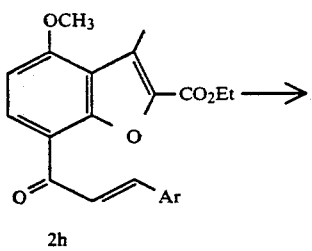
2h

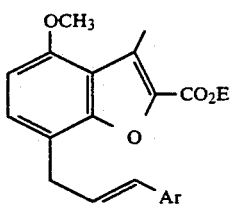
2d

Access to comparable arylalkenyls is shown in Scheme 2.

In Scheme 2 methylation of 1a followed by Vilsmeier formylation results in Compound 2b. Addition of aryl acetate followed by elimination and decarboxylation (according to the method of Lazer) results in 2d. U.S. Pat. No. 4,743,606 issued to Lazer on May 10, 1988, is hereby incorporated by reference. See also J. Med. Chem. (1989), 32, 100–104. Demethylation with pyridinium hydrochloride and decarboxylation with copper/quinoline results in 2e. Where desired, the arylalkenyl group may be saturated to provide access to an additional series of arylalkyls.

An alternative to the above described Vilsmeier route, Friede Craft's addition to 2b with acetyl chloride followed by addition according to Lazer (supra) results in 2h. Subsequent reduction using sodium borohydride in isopropyl alcohol results in 2d. Demethylation and decarboxylation of 2d results in 2e as indicated above.

Regardless of route, the resulting phenols such as 2e and 2f may be 5-alkylated with allyl bromide and rearranged (Claisen) thermally to give the desired product.

Scheme 3

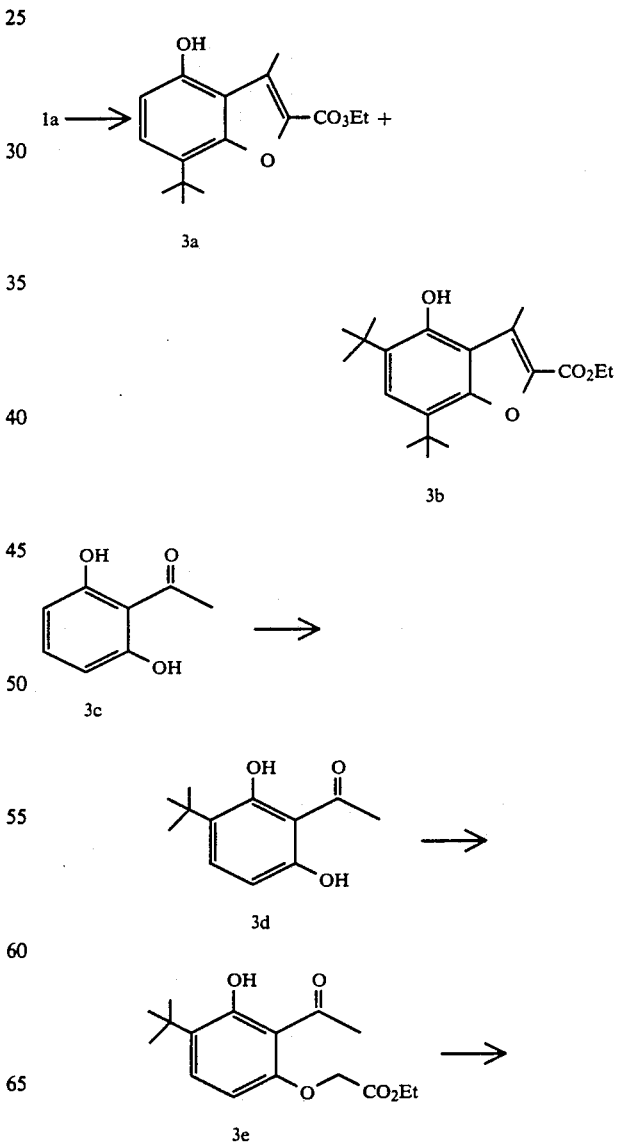

Scheme 3

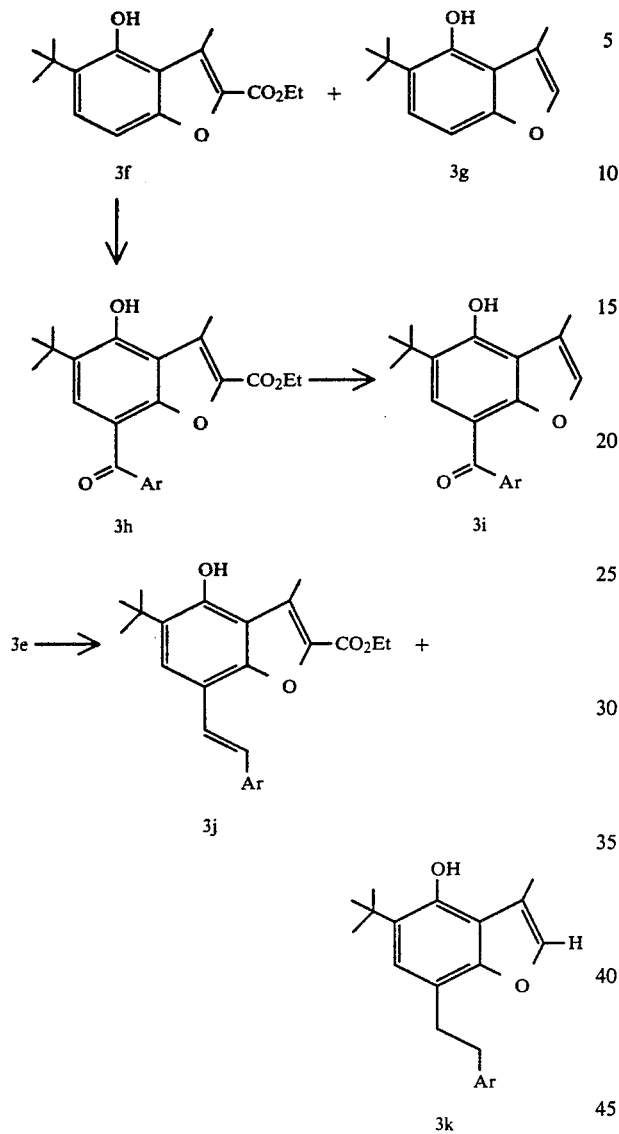

Scheme 4

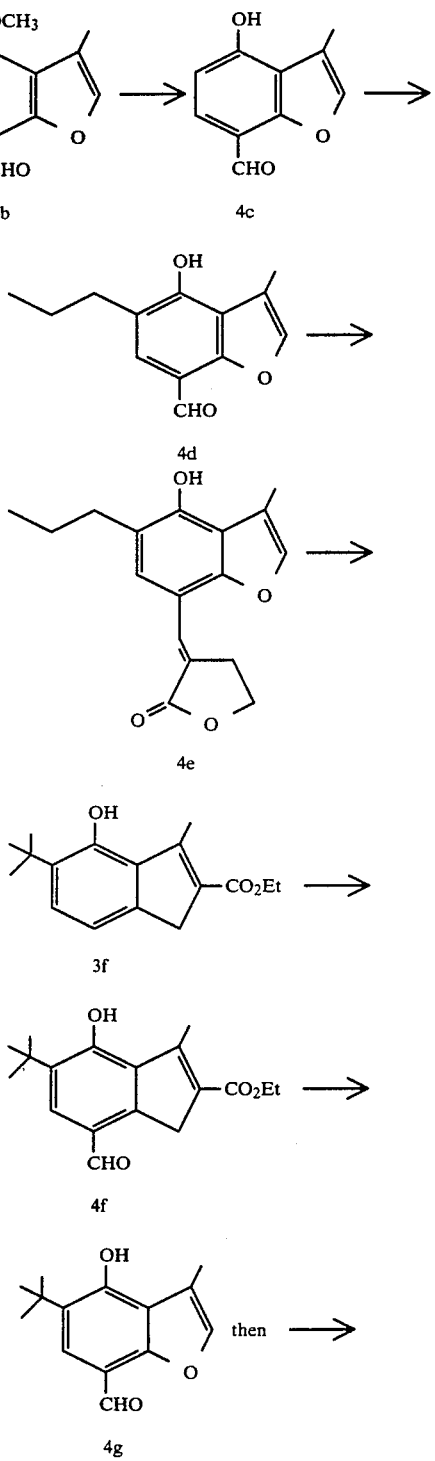

The preparation of the 5-tert-butyl analogs is shown in Scheme 3. Direct tert-butylation of 1a afforded 3a and 3b. Such compounds were saponified and decarboxylated by standard means. Electrophilic alkylation of 3c gave the tert-butyl compound 3d. Alkylation of 3d with bromoethyl acetate occurred exclusively at the phenolic hydroxyl distal to the alkyl group to afford 3e. Cyclization of 3e (such as with NaOEt, EtOH) gave 3f along with a small amount of the decarboxylated analog 3g. Acylation of 3f with aroyl halides, using aluminium chloride as catalyst, in 1,2-dichloroethane results in the formation of the desired ketones, compounds such as those described in Examples 13, 15 and 17. Saponification and decarboxylation, in the usual manner, provided the final compounds, such as those described in Examples 14, 16 and 19.

Compound 3e also provides a starting point for access to the 5-(t-butyl)-7-arylalkenyl analogs. By starting with 3e and then following the reaction steps depicted in Scheme 2, beginning with the Vilsmeier formylation, one obtains compounds such as 3j and 3k.

-continued
Scheme 4

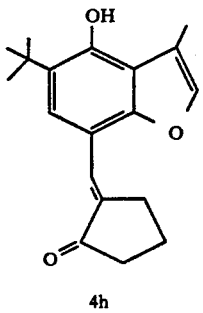

4h

Access to 7-exo-enyl compounds as shown in Scheme 4. Compound 4a is first converted to the acid and then decarboxylated by reaction with copper/quinoline to yield 4b. 4b is then demethylated to 4c. Reaction of 4c with allylbromide, followed by Claisen (thermal) rearrangement and reduction results in 4d. Aldol condensation or alternatively Wittig reaction of 4a according to the method of Katsumi et al, results in 4e. U.S. Pat. No. 4,431,656 issued to Katsumi et al on Feb. 14, 1984, is hereby incorporated by reference. See also Chem. Pharm. Bull. (1986) 4, 1619–1627.

In a similar manner, Vilsmeier formylation of 3f followed by decarboxylation of 4f leads to Compound 4g. Subsequent conversion according to the method of Katsumi et al leads to 4h.

This invention also relates to a method of treating inflammation in patients in need of such treatment. Generally, an effective non-toxic amount of a compound of formula I or a pharmaceutical composition thereof, particularly an especially preferred compound, is administered to the patient as the active constituent.

To demonstrate the utility of the present invention, representative novel compounds of formula I were evaluated for their ability to inhibit production of $LTB_4$ in PMN derived from male Sprague-Dawley rats. Compounds of formula I were also evaluated in accordance with the ram seminal vesicle microsomal cyclooxygenase (RSV CO) assay. Compounds displaying activity in the CO assay include indomethacin and ibuprofen.

As indicated below representative compounds within the scope of the present invention have been found to possess in vitro activities superior to those of the above reference prior art compounds in standard pharmaceutical assays as described below.

PMN $LTB_4$ Assay

Male Sprague-Dawley rats (~350 g) were injected intraperitoneally the day before use with 8 mL of 12% sodium caseinate. The next day the animals were killed by $CO_2$ asphyxiation and the peritoneal cavity lavaged twice with 20 mL of Hanks balanced salts containing 15 mM HEPES (pH 7.4), 1.4 mM $Ca^{++}$ and 0.7 mM $Mg^{++}$ (Hepes-Hanks). The suspensions were filtered through plastic mesh and centrifuged at 260×g for 5 minutes. The cells were resuspended in 50 ml Hepes-Hanks and recentrifuged. The PMN pellets were combined and suspended at $1.25 \times 10^7$ cells/mL. The cell suspension was diluted 1:10, preincubated 5 minutes at 37° and distributed into 96 well microtiter plates with 200 mL/well. The wells had previously received samples, controls, ect., in 25 mL of 0.001% fatty acid free BSA in Hepes-Hanks. The plates were incubated 2 min. at 37° and then the cells were stimulated to produce $LTB_4$ by the addition of 25 mL of 100 mM A23187. After 4 minutes the plates were frozen in dry ice. The frozen plates were thawed to 4° and 25 mL aliquots removed to V-well plates. Antibody to $LTB_4$ (50 mL) was added in and after 15 minutes at room temperature, 50 mL of $^3H$-$LTB_4$ was added and the plates were stored overnight at 4° to allow equilibration. The next day the "free" $3HLTB_4$ was removed by adsorption to dextran coated charcoal (90 mL/well of a 4% charcoal suspension with 0.25% Dextran T-70 in 10 mM potassium phosphate (pH 7.3) containing 1 mM EDTA and 0.25 mM thimerasol) durring a 10 minute ice temperature incubation. The charcoal was removed by a 10 minute centrifugation at 260×g. Aliquots of the supernatant were counted in a Packard 460, analyzed in a Masscomp computer (programs "filhariala and fhariasa") and the data reported as percent inhibition of $LTB_4$ production.

Ram Seminal Vesicle Microsomal Cyclooxygenase Assay (RSV CO)

Ram seminal vesicular glands were trimed of excess fat, 50 gm diced into ice cold 0.1M potassium phosphate (pH 7.6) buffer and homoginized using a Brinkman Polytron. The suspension was centrifuged 10 min. at 10K×g (4°) and the supernatant filtered through two cheesecloth layers. The filtrate was centrifuged 160 min. at 105K×g. The supernatant was discarded and the pellet surface rinsed with a small volume of buffer. The pellets were combined in a small volume, briefly homoginized with the Polytron and frozen in 0.5 mL aliquots at −80°. The protien concentration was ~50 mg/mL. The thawed enzyme was diluted 1:63 with 0.125M sodium EDTA (pH 8.0) containing 50 mg/mL. The thawed enzyme was diluted 1:63 with 0.125M sodium EDTA (pH 8.0) containing 50 mg/ml BSA. A substrate cofactor premix was prepared with 66 mL 14C-arachidonic acid (~20K cpm/12.5 mL) in 500 mL 0.125M sodium EDTA (pH 8.0) plus 10 mL 50 mM hydroquinone and 10 mL 200 mM glutathione. To each sample well in the 96 well plate agents were added disolved in 0.5 mL DMSO followed by 12.5 mL of the diluted enzyme. After a 4 minute preincubation at room temperature 12.5 mL of the substrate cofactor mix was added to start the reaction. The reaction was killed after 20 minutes at room temperature by adding 25 mL methanol containing 200 mg PGE2 and 400 mg AA per mL. The entire reaction mixture was spotted onto a preadsorbent silica gel GF thin layer plate and, after air drying 45 minutes developed 12 cm in ethyl acetate:glacial acetic acid (99:1). The developed lanes were scanned for the distribution of radiolabel using a Bioscan Imaging Detector and the integrated peaks compared to standards and controls yielding percent inhibition.

TABLE I

Inhibition of Leukotriene Biosynthesis in Rat PMN and Prostaglandin Biosynthesis in RSV Cyclooxygenase by 5,7-Disubstituted-3-Methyl-4-Hydroxy-Benzofurans.

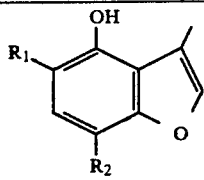

| compd | $R_1$ | $R_2$ | CO IC50(mM)* | RatPMN (LO) IC50(mM)* | mp, °C. | formula | anal |
|---|---|---|---|---|---|---|---|
| 3 | H | 2-thienoyl | 0.8 | 2.7 | 145–148 | $C_{14}H_{10}O_3S$ | C,H,S |
| 6 | H | benzoyl | 1.3 | 3.5 | 176–178 | $C_{16}H_{12}O_3$ | C,H |
| 4 | allyl | 2-thienoyl | 5.6 | 6.7 | 121–124 | $C_{17}H_{14}O_3S$ | C,H,S |
| 5 | n-propyl | 2-thienoyl | 1.3 | 1.7 | 127–128 | $C_{17}H_{16}O_3S$ | C,H,S |
| 10a | H | t-butyl | a | 2.1 | 96–98 | $C_{13}H_{16}O_2$ | C,H |
| 10b | t-butyl | t-butyl | b | c | 99–101 | $C_{17}H_{24}O_2$ | C,H |
| 12b | t-butyl | H | 54 | 0.6 | 79–81 | $C_{13}H_{16}O_2$ | C,H |
| 14 | t-butyl | 2-thienoyl | 1.0 | 1.5 | 131–133 | $C_{18}H_{18}O_3S$ | C,H,S |
| 16 | t-butyl | benzoyl | 1.3 | 1.1 | 138–140 | $C_{20}H_{20}O_3$ | C,H |
| 19 | t-butyl | p-Cl-benzoyl | 1.2 | 4.4 | 131–138 | $C_{20}H_{19}O_2Cl$ | C,H,Cl |

$^a$1% inhibition at 1 mg/ml
$^b$0% inhibition at 10 mg/ml
$^c$37% inhibition at 1 mg/ml
*IC$_{50}$'s are mean values of at least two titrations.

For the treatment of inflammation, pain, fever, rheumatoid arthritis, osteoarthritis, bronchial inflammation, inflammatory bowel disease, asthma, allergic disorder, skin diseases, cardiovascular disorder, glaucoma, emphysema, acute respiratory distress syndrome, spondylitis, lupus, gout, and psoriasis or other diseases mediated by prostaglandins, a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscluar, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lonzenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelation or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Preferably, the compounds of the invention are administered topically, by inhalation spray or rectally in dosage unit formulations containing convention nontoxic pharmaceutically acceptable carriers, adjuvants and vehicles.

The pharmaceutical compositions containing one or more compounds of formula (I) are suitable for topical use when they are in the form of aqueous or oily solutions or suspensions, dispersible powders or granules, tinctures, topical aerosol emulsions, creams, ointments, jellies, suppositories or the like. These topical compositions may be prepared according to any method known to the art.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial ester derived from fatty acids and hexitol anhydrides, for example, polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally-occurring phosphatides, for example, soy bean, lecithin, and esters or partial ester derived from fatty acids and hexitol anhydries, for example, sorbitan mono-oleate, and condensation products of the said partial esters with enthylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sevacate, ethyl carproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above-indicated condition (10 mg to 7 gms per patient per day). For example, inflammation is effectively treated by the administration from about 0.5 to 50 mg of the compound per kilogram of body weight per day (25 mg to 5 gms per patient per day).

The amount of active ingredient that may be combined with the carrier materials to produce a single dosage form will vary depending upon the host treated and the particular mode of administration. Dosage unit forms will generally contain between from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate the preparation of the compounds of the formula (I) and as such are not to be considered as limiting the invention set forth in the claims appended hereto.

General

All reagents and solvents were analytical reagent grade and were used without further purification unless otherwise noted. Routine $^1$H Nuclear magnetic resonance (NMR) spectra were obtained on a Varian XL 200 instrument as solutions in deuterochloroform using tetramethylsilane (TMS, d 0.00) as internal standard. Infrared (IR) spectra were generally obtained as solutions in chloroform on a Perkin Elmer 1310 spectrophotometer. Low resolution mass spectra (MS-1r) were obtained on an LKB Model 9000 mass spectrometer at an ionizing voltage of 70 eV. Melting points were obtained on a Thomas-Hoover melting point apparatus and are uncorrected. Microanalyses were performed at the Merck analytical laboratory. Flash chromatography was performed essentially as described in the literature using Kieselgel 60 (EM Science, 230–400 mesh) as stationary phase. Preparative HPLC refers to separations performed on a Waters PrepLC 500A instrument using Waters PrepPAK-500/SILICA cartridges as stationary phase. Analytical thin layer chromato-graphy (TLC) was performed using Silica gel GHLF plates of 0.25 mm thickness obtained from Analtech Inc.

EXAMPLE 1

Ethyl 3-Methyl-4-methoxy-7-(2-thienoyl)benzofuran-2-carboxylate (1)

To a solution of ethyl 3-methyl-4-hydroxybenzofuran-2-carboxylate 20 (5.02 g, 22.8 mmol) in acetone (85 mL) was added sequentially $K_2CO_3$ (6.3 g, 45.6 mmol) and methyl iodide (6.47 g, 45.6 mmol). The resulting suspension was heated to reflux with stirring for 15 hours, allowed to cool, diluted with water (125 mL), and acidified with 2N HCl (50 mL). The resulting mixture was extracted with ethyl acetate (1×100 mL then 2×50 mL) and the combined extracts were dried and concentrated to a brown oil. Chromatographic purification (Preparative HPLC, 5% ethyl acetate in hexane as eluant) afforded pure ethyl 3-methyl-4-methoxybenzofuran-2-carboxylate as a colorless oil which crystallized on standing. mp 67°–69° C.; $^1$H NMR d 1.47 (3H, t, J=6 Hz), 2.78 (3H, s), 3.96 (3H, s), 4.48 (2H, q, J=6 Hz), 6.66 (1H, d, J=8 Hz), 7.16 (1H, d, J=8 Hz), 7.36 (1H, t, J=8 Hz).

To a solution of ethyl 3-methyl-4-methoxy-benzofuran-2-carboxylate (3.48 g, 14.86 mmol) in dry 1,2-dichloroethane (15 mL) was added a solution of thiophene-2-carbonyl chloride (6.54 g, 44.61 mmol) in 1,2-dichloroethane (10 mL) followed by the portionwise addition of aluminum chloride (7.92 g, 59.40 mmol). An exothermic reaction ensued and the mixture was allowed to stir until gas evolution had slowed, then warmed to reflux for 2 hours. Upon cooling the reaction mixture was poured into 2N HCl (100 mL) and extracted with methylene chloride (4×25 mL). The combined organic extracts were washed with 5% NaHCO₃, dried (Na₂SO₄), and concentrated to a brown solid (5.40 g). Recrystallization from ethanol/benzene afforded pure ethyl 3-methyl-4-methoxy-7-(2-thienoyl)benzofuran-2-carboxylate, compound 1. mp 179°–182° C.; ¹H NMR d 1.40 (3H, t, J=6 Hz), 2.77 (3H, s), 4.04 (3H, s), 4.42 (2H, q, J=6 Hz), 6.75 (1H, d, J=8 Hz), 7.17 (1H, dd, J=4 Hz), 7.72 (2H, m), 7.86 (1H, d, J=8 Hz).

EXAMPLE 2

3-Methyl-4-methoxy-7-(2-thienoyl)benzofuran-2-carboxylic acid (2)

To a solution of potassium hydroxide (1.96 g, 34.86 mmol) in water (75 mL) was added compound 1 (4.00 g, 11.62 mmol) and the resulting suspension was heated to reflux for two hours. During the reflux a small portion of methanol was rinsed into the reaction mixture. After cooling, the reaction mixture was diluted with water (225 mL) and acidified with 2N HCl (25 mL). The resulting suspension was cooled in an ice bath, and the product collected by filtration. After vacuum drying, 3-methyl-4-methoxy-7-(2-thienoyl)-benzofuran-2-carboxylic acid, compound 2, was obtained. mp 252°–255° C.; ¹H NMR d 2.80 (3H, s), 2.80 (1H, br s), 4.06 (3H, s), 6.76 (1H, d, J=8 Hz), 7.19 (1H, m), 7.70 (1H, dd, J=4 Hz, 1 Hz), 7.76 (1H, dd, J=4 Hz, 1 Hz), 7.90 (1H, d, J=8 Hz).

EXAMPLE 3

3-Methyl-4-hydroxy-7-(2-thienoyl)benzofuran (3)

An intimate mixture of compound 2 (3.50 g, 11.0 mmol), quinoline (7 mL), and copper powder (0.70 g, 11.0 mol) was carefully heated to 210° C. and maintained at that temperature until gas evolution ceased (about 10 minutes). The resulting mixture was cooled to 80° C. and poured into 1N HCl (120 mL). Chloroform (50 mL) was added and the mixture stirred for 5 minutes and filtered through a pad of celite. The pad was washed with an additional portion of chloroform (25 mL). The organic layer was separated and the aqueous layer extracted with additional portions of chloroform (2×50 mL). The combined organic extracts were dried (Na₂SO₄) and concentrated. The crude product was purified by preparative HPLC using 15% ethyl acetate in hexane as eluant to afford 3-methyl-4-methoxy-7-(2-thienoyl)benzofuran. mp 131°–134° C.; ¹H NMR d 2.40 (3H, d, J=1 Hz), 4.02 (3H, s), 6.71 (1H, d, J=8 Hz), 7.17 (1H, m), 7.38 (1H, d, J=1 Hz), 7.70 (3H, m).

A solution of freshly prepared pyridinium hydrochloride (4.84 g, 41.9 mmol) and 3-methyl-4-methoxy-7-(2-thienoyl)benzofuran (2.30 g, 8.38 mmol) in quinoline (10 mL) was heated to reflux for 2.5 hours. The mixture was cooled, an additional portion of pyridinium hydrochloride added (2.42 g, 20.9 mmol) and reflux was resumed for one hour. After cooling the reaction mixture was poured into water (200 mL) and acidified with 2N HCl. The resulting mixture was extracted with chloroform (5×50 mL) and the combined organic extracts were washed with water (50 mL), dried (Na₂SO₄), and concentrated. Chromatographic purification by preparative HPLC using 25% ethyl acetate in hexane as eluant afforded 3-methyl-4-hydroxy-7-(2-thienoyl)benzofuran compound 3 along with recovered starting material. A sample of the desired product was recrystallized from ether/hexane. ¹H NMR d 2.45 (3H, s), 6.24 (1H, br s), 6.45 (1H, d, J=8 Hz), 7.17 (1H, dd, J=4 Hz, 4 Hz), 7.37 (1H, s), 7.61 (1H, d, J=8 Hz), 7.67 (1H, d, J=4 Hz), 7.75 (1H, d, J=4 Hz).

| Micro analysis for compound 3: | C | H | S |
|---|---|---|---|
| Calc'd: | 65.10 | 3.90 | 12.4 |
| Found: | 65.15 | 4.20 | 12.1 |

EXAMPLE 4

3-Methyl-4-(2-propen-1-yl)oxy-7-(2-thienoyl)benzofuran (4)

To a solution of compound 3 (0.50 g, 1.92 mmol) in acetone (10 mL) was added sequentially potassium carbonate (0.53 g, 3.84 mmol) and allyl bromide (0.47 g, 3.84 mmol). The mixture was heated to reflux for two hours, cooled, diluted with water (50 mL), and acidified with 2N HCl. The aqueous mixture was extracted with methylene chloride (3×25 mL) and the combined extracts dried (Na₂SO₄) and concentrated to an oil. The crude 3-methyl-4-allyloxy-7-(2-thienoyl)benzofuran thus obtained was sufficiently pure for further synthesis. ¹H NMR d 2.44 (3H, d, J=2 Hz), 4.74 (2H, d, J=4 Hz), 5.44 (2H, m), 6.12 (1H, m), 6.71 (1H, d, J=8 Hz), 7.15 (1H, m), 7.36 (1H, d, J=2 Hz), 7.68 (3H, m).

A solution of 3-methyl-4-allyloxy-7-(2-thienoyl)benzofuran (0.43 g, 1.44 mmol) in 1,3-dichlorobenzene (4 mL) was heated to reflux under nitrogen for five hours. The reaction mixture was cooled and the product purified by preparative HPLC, using 10% ethyl acetate in hexane as eluant, to afford 3-methyl-4-hydroxy-5-(2-propen-1-yl)-7-(2-thienoyl)benzofuran, compound 4. An analytical sample was obtained by recrystallization from ether/hexane. ¹H NMR d 2.43 (3H, d, J=2 Hz), 3.54 (2H, d, J=6 Hz), 5.30 (2H, m), 5.86 (1H, s), 6.10 (1H, m), 7.16 (1H, dd, J=4 Hz, 4 Hz), 7.34 (1H, d, J=2 Hz), 7.50 (1H, s), 7.65 (1H, d, J=4 Hz), 7.72 (1H, d, J=4 Hz).

| Micro analysis for compound 4: | C | H | S |
|---|---|---|---|
| Calc'd: | 68.44 | 4.73 | 10.75 |
| Found: | 68.26 | 4.96 | 10.89 |

EXAMPLE 5

3-Methyl-4-hydroxy-5-propyl-7-(2-thienoyl)benzofuran (5)

A mixture of 3-methyl-4-hydroxy-5-(2-propen-1-yl)-7-(2-thienoyl)benzofuran, compound 4 (0.228 g, 0.76 mmol) and 5% Pd/C (0.020 g) in absolute ethanol (5 mL) was hydrogenated at 3 atmospheres pressure. After 0.5 hours the requisite amount of hydrogen had been taken up. The catalyst was removed by filtration through celite and the filtrate concentrated to an oil that slowly solidified. Recrystallization of this material from ether/hexane afforded pure 3-methyl-4-hydroxy-5-propyl-7-(2-thienoyl)benzofuran, compound 5 as an off white solid. ¹H NMR d 0.98 (3H, t, J=8 Hz), 1.67 (2H, m), 2.40 (3H, s), 2.64 (2H, t, J=6 Hz), 7.14 (1H, m), 7.30 (1H, s), 7.48 (1H, s), 7.63 (1H, d, J=4 Hz), 7.68 (1H, d, J=4 Hz).

| Micro analysis for compound 5: | C | H | S |
|---|---|---|---|
| Calc'd: | 67.98 | 5.37 | 10.68 |

| Micro analysis for compound 5: | C | H | S |
|---|---|---|---|
| Found: | 67.81 | 5.20 | 10.52 |

EXAMPLE 6

3-Methyl-4-hydroxy-7-benzoylbenzofuran (6)

To a solution of ethyl 3-methyl-4-methoxybenzofuran-2-carboxylate (1.00 g, 4.27 mmol) and benzoyl chloride (1.80 g, 12.81 mmol) in 1,2-dichloroethane (12 mL) was added aluminum chloride (1.71 g, 12.81 mmol) in portions. The mixture was heated to reflux for 1.5 hours then allowed to cool and poured into 2N HCl (50 mL). The resulting mixture was extracted with methylene chloride (3×30 mL) and the combined extracts washed with saturated NaHCO$_3$ (3×25 mL), dried (Na$_2$SO$_4$), and concentrated. The crude product was purified by preparative HPLC, using 25% ethyl acetate in hexane as eluant, to afford ethyl 3-methyl-4-methoxy-7-benzoylbenzofuran-2-carboxylate mp. 137°–139° C.; $^1$H NMR d 1.27 (2H, t, J=6 Hz), 2.67 (3H, s), 3.95 (3H, s), 4.28 (2H, q, J=6 Hz), 6.66 (1H, d, J=8 Hz), 7.44 (3H, m), 7.72 (3H, m).

A mixture of ethyl 3-methyl-4-methoxy-7-benzoylbenzofuran-2-carboxylate (1.10 g, 3.25 mmol) and freshly fused pyridinium hydrochloride (2.14 g, 18.52 mmol) was heated to 195° C. for 45 minutes. After cooling, the reaction mixture was diluted with 2N HCl (25 mL) and extracted with ethyl acetate (3×25 mL). The combined extracts were washed with water (2×20 mL), dried (Na$_2$SO$_4$), and concentrated. Flash chromatography, using 20% ethyl acetate in hexane as eluant, afforded 3-methyl-4-hydroxy-7-benzoylbenzofuran 6. $^1$H NMR d 2.44 (3H, s), 6.06 (1H, br s), 6.65 (1H, d, J=8 Hz), 7.36 (1H, s), 7.54 (4H, m), 7.84 (2H, m).

| Micro analysis for compound 6: | C | H | S |
|---|---|---|---|
| Calc'd: | 74.99 | 5.03 | |
| Found: | 75.18 | 4.83 | |

EXAMPLE 7

Ethyl 3-Methyl-4-hydroxy-7-tert-butylbenzofuran-2-carboxylate (7a) and Ethyl 3-Methyl-4-hydroxy-5,7-di-tert-butylbenzofuran-2-carboxylate (7b)

To a solution of ethyl 3-methyl-4-hydroxybenzofuran-2-carboxylate, 4 (1.00 g, 4.54 mmol) and tert-butanol (1.00 g, 13.49 mmol) in benzene (30 mL) at 5° C. was added conc H$_2$SO$_4$ (1 mL). The bottle was sealed and the mixture allowed to stir at room temperature for 45 minutes before quenching by the addition of saturated NaHCO$_3$ (50 mL). The resulting mixture was extracted with ethyl acetate (2×50 mL) and the combined organic extracts were dried (Na$_2$SO$_4$) and concentrated. Preparative HPLC, using 10% ethyl acetate in hexane as eluant, afforded ethyl 3-methyl-4-hydroxy-7-tert-butylbenzofuran-2-carboxylate, compound 7a as a white solid. mp 186°–189° C.; $^1$H NMR d 1.46 (3H, t, J=6 Hz), 1.49 (9H, s), 2.80 (2H, q, J=6 Hz), 6.52 (1H, d, J=8 Hz), 7.14 (1H, d, J=8 Hz) and ethyl-3-methyl-4-hydroxy-5,7-di-tert-butylbenzofuran-2-carboxylate 7b as a white solid mp 162°–164° C. from hexane; $^1$H NMR d 1.45 (3H, t, J=6 Hz) 1.51 (9H, s), 1.51 (9H, s), 2.84 (3H, s), 4.44 (2H, q, J=6 Hz), 5.32 (1H, br s), 7.27 (1H, s).

EXAMPLE 8

3-Methyl-4-hydroxy-7-tert-butylbenzofuran-2-carboxylic acid (8)

Ethyl 3-methyl-4-hydroxy-7-tert-butylbenzofuran (0.405 g, 1.47 mmol) was saponified in a solution of KOH (0.247 g, 4.41 mmol) in refluxing water (10 mL) for two hours. Acidification of the cooled mixture led to precipitation of the product. 3-Methyl-4-hydroxy-7-tert-butylbenzofuran-2-carboxylic acid, compound 8, was collected by filtration and vacuum dried. This material was decarboxylated without further purification, mp 219°–222° C.; $^1$H NMR (DMSO-d$_6$) d 1.38 (9H, s), 2.64 (3H, s), 6.55 (1H, d, J=8 Hz), 7.07 (1H, d, J=8 Hz), 9.66 (1H, s).

EXAMPLE 9

3-Methyl-4-hydroxy-5,7-di-tert-butylbenzofuran-2-carboxylic acid (9)

Ethyl 3-methyl-4-hydroxy-5,7-di-tert-butylbenzofuran-2-carboxylate (0.475 g, 1.43 mmol) was refluxed in a solution of KOH (0.241 g, 4.29 mmol) in water (10 mL) and methanol (2 mL) for two hours. Acidification of the cooled mixture led to precipitation of the product. 3-Methyl-4-hydroxy-5,7-di-tert-butylbenzofuran-2-carboxylic acid, compound 9, was collected by filtration and vacuum dried. This material was decarboxylated without further purification. mp 241°–243° C.; $^1$H NMR (DMSO-d$_6$) d 1.40 (18H, s), 2.71 (3H, s), 7.18 (1H, s), 8.35 (1H, s).

EXAMPLE 10

3-Methyl-4-hydroxy-7-tert-butylbenzofuran (10a) and 3-Methyl-4-hydroxy-5,7-di-tert-butylbenzofuran (10b)

A mixture of 3-methyl-4-hydroxy-7-tert-butylbenzofuran-2-carboxylic acid (0.250 g, 1.0 mmol), quinoline (0.75 mL), and copper powder (0.064 g, 1.0 mmol) was heated to 210° C. until gas evolution ceased (about 10 minutes) and then poured into 2N HCl (15 mL). Carbon tetrachloride (15 mL) was added and the biphasic mixture was filtered through celite. The layers were separated and the aqueous layer extracted with an additional portion of carbon tetrachloride (15 mL). The combined extracts were dried (Na$_2$SO$_4$) and concentrated. Flash chromatography using 10% ethyl acetate in hexane as eluant afforded 3-methyl-4-hydroxy-7-tert-butylbenzofuran, compound 10a. Recrystallization from hexane provided analytically pure material. $^1$H NMR d 1.46 (9H, s), 2.43 (3H, s), 6.49 (1H, d, J=8 Hz), 6.98 (1H, d, J=8 Hz), 7.36 (1H, s).

A mixture of 3-methyl-4-hydroxy-5,7-di-tert-butylbenzofuran-2-carboxylic acid (0.350 g, 1.14 mmol), quinoline (1.0 mL), and copper powder (0.072 g 1.14 mmol) was heated to 210° C. until gas evolution had ceased. The mixture was cooled, diluted with ethyl acetate (30 mL) and poured into 2N HCl. The biphasic mixture was filtered through a celite pad and the layers separated. The aqueous layer was extracted with ethyl acetate (50 mL) and the combined organic layers dried (Na$_2$SO$_4$) and concentrated. Flash chromatography afforded 3-methyl-4-hydroxy-5,7-di-tert-butylbenzofuran, compound 10b. $^1$H NMR d 1.46 (9H, s), 1.49 (9H, s), 2.46 (3H, s), 5.12 (1H, s), 7.11 (1H, s), 7.29 (1H, s).

| Micro analysis for compound 10a: | C | H |
| --- | --- | --- |
| Calc'd: | 76.44 | 7.90 |
| Found: | 76.64 | 8.14 |

| Micro analysis for compound 10b: | C | H |
| --- | --- | --- |
| Calc'd: | 78.42 | 9.29 |
| Found: | 78.44 | 9.39 |

EXAMPLE 11

2,6-Dihydroxy-3-tert-butylacetophenone (11a) and Ethyl 2-(2-acetyl-3-hydroxy-4-tert-butylphenoxy)-acetate (11b)

A mixture of 2,6-dihydroxyacetophenone (2.00 g, 13.15 mmol), tert-butanol (1.46 g, 19.73 mmol), and concentrated $H_2SO_4$ (0.3 mL) in benzene (50 mL) was heated to 55° C. in a sealed pressure bottle for 4 hours. The mixture was cooled, diluted with ethyl acetate (50 mL) and the resulting mixture washed with 5% $NaHCO_3$, dried ($Na_2SO_4$), and concentrated. Preparative HPLC afforded 2,6-dihydroxy-3-tert-butylacetophenone 11a which was sufficiently pure for further chemistry. mp 183°–186° C.; $^1H$ NMR d 1.36 (9H, s), 2.72 (3H, s), 5.72 (1H, s), 6.16 (1H, d, J=8 Hz), 7.24 (1H, d, J=8 Hz).

To a solution of 2,6-dihydroxy-3-t-butylacetophenone, compound 11a (1.25 g, 6.00 mmol) in acetone (30 mL) was added potassium carbonate (1.66 g, 12.00 mmol) followed by ethyl bromoacetate (1.00 g, 6.00 mmol) and the stirred mixture heated to reflux for 75 minutes. The cooled mixture was poured into water (60 mL) and acidified with 2N HCl. The reaction mixture was then extracted with ethyl acetate (40 mL), dried ($Na_2SO_4$) and concentrated. Preparative HPLC, using 10% ethyl acetate in hexane as eluant, afforded ethyl 2-(2-acetyl-3-hydroxy-4-tert-butylphenoxy)acetate, compound 11b as a yellow solid sufficiently pure for further chemistry. mp 67°–68° C.; $^1H$ NMR d 1.32 (3H, t, J=6 Hz), 1.38 (9H, s), 2.82 (3H, s), 4.30 (2H, q, J=6 Hz), 4.68 (2H, s), 6.16 (1H, d, J=8 Hz), 7.14 (1H, d, J=8 Hz).

EXAMPLE 12

Ethyl 3-Methyl-4-hydroxy-5-tert-butylbenzofuran-2-carboxylate (12a) and 3-Methyl-4-hydroxy-5-tert-butylbenzofuran (12b)

To a solution of sodium ethoxide freshly prepared from sodium metal (0.104 g, 4.50 mmol) in ethanol (25 mL) was added ethyl 2-(2-acetyl-3-hydroxy-4-tert-butylphenoxy)acetate 11b (1.26 g, 4.28 mmol) and the mixture heated to reflux for 10 minutes. The reaction mixture was cooled and acidified by pouring into 2N HCl (75 mL). The resulting solution was extracted with ethyl acetate (2×35 mL) and the combined extracts dried ($Na_2SO_4$), and concentrated. Flash chromatography afforded, in order of elution 3-methyl-4-hydroxy-5-tert-butylbenzofuran, compound 12b. mp 79°–81° C.; $^1H$ NMR d 1.49 (9H, s), 2.48 (3H, s), 5.27 (1H, s), 7.00 (1H, d, J=8 Hz), 7.24 (1H, d, J=8 Hz), 7.26 (1H, s) and ethyl 3-methyl-4-hydroxy-5-tert-butylbenzofuran-2-carboxylate, compound 12a, mp. 109–112 (from hexane); $^1H$ NMR d 1.42 (3H, J=6 Hz), 1.46 (9H, s), 2.83 (3H, s), 4.43 (2H, q, J=6 Hz), 5.45 (1H, br s), 7.04 (1H, d, J=8 Hz), 7.37 (1H, d, J=8 Hz).

| Micro analysis for compound 12b: | C | H |
| --- | --- | --- |
| Calc'd: | 76.44 | 7.90 |
| Found: | 76.44 | 7.91 |

EXAMPLE 13

Ethyl-3-methyl-4-hydroxy-5-tert-butyl-7-(2-thienoyl)-Benzofuran-2-Carboxylate (13)

To a solution of ethyl-3-methyl-4-hydroxy-5-tert-butyl-benzofuran-2-carboxylate 12a (0.760 g, 2.75 mmol) in 30 mL dry (4A sieves) 1,2-dichloroethane at 5° C. under nitrogen was added a solution of thiophene-2-carbonyl-chloride (806 mg, 5.49 mmol) in 5 mL 1,2-dichloroethane followed by the portionwise addition of $AlCl_3$ (0.733 g, 5.59 mmol). The cooling bath was removed and the reaction mixture allowed to warm to room temperature and then refluxed for 1.5 hours. The reaction mixture was then cooled and poured into 100 mL ice cold 2N HCl. The organic layer was removed and the aqueous layer extracted with methylene chloride (3×30 mL). The combined organic layers were washed with 5% $NaHCO_3$ (50 mL), water (50 mL) and saturated NaCl (50 mL) and dried over $Na_2SO_4$. Concentration followed by flash chromatography (30% EtOAc in hexane) afforded compound 13 as an oil sufficiently pure for further use; $^1H$ NMR d 1.41 (3H, t, J=6 Hz), 1.55 (9H, s), 2.90 (3H, s), 4.42 (2H, q, J=6 Hz), 7.19 (1H, dd, J=4 Hz), 7.75 (2H, d, J=4 Hz), 7.90 (1H, s).

EXAMPLE 14

3-Methyl-4-hydroxy-5-tert-butyl-7-(2-thienoyl)-benzofuran (14)

To a solution of KOH (0.18 g, 3.21 mmol) in 8.0 mL water and 3.0 mL methanol was added ethyl-3-methyl-4-hydroxy-5-tert-butyl-7-(2-thienoyl)-benzofuran-2-carboxylate, compound 13 (0.412 g, 1.07 mmol). The reaction mixture was heated to reflux for 0.5 hours. The resulting solution was cooled in an ice bath and acidified by the dropwise addition of 2N HCl. The acid was collected by filtration, washed with water and pulled dry over night on the filter funnel to give desired product sufficiently pure for further use. mp 145° C. with decarboxylation; $^1H$ NMR (DMSO-$d_6$) d 1.44 (9H, s), 2.76 (3H, s), 7.17 (1H, dd, J=4 Hz), 7.73 (2H, d, J=4 Hz), 7.90 (1H, s).

To a solution of 3-methyl-4-hydroxy-5-tert-butyl-7-(2-thienoyl)-benzofuran-2-carboxylic acid (0.345 g, 0.96 mmol) in quinoline (1.0 mL) at room temperature was added fine copper powder (0.061 g, 0.96 mmol). The reaction mixture was flushed with nitrogen and heated in an oil bath to 200° C. until all $CO_2$ evolution had ceased (about 20 min.). The reaction mixture was cooled to room temperature and poured into 30 mL 2N HCl. The aqueous solution was extrated with EtOAc (3×15 mL). The combined organic extracts were washed with 2N HCl (2×10 mL), water (10 mL) and saturated NaCl (10 mL) and dried over $Na_2SO_4$. Filtration, concentration and flash chromatography (85:15, hexane:EtOAc) afforded pure compound 14. $^1H$ NMR d 1.5 (9H, s), 2.5 (3H, s), 5.74 (1H, s), 7.18 (1H, dd, J=4 Hz), 7.34 (1H, s), 7.68 (1H, d, J=4 Hz), 7.73 (1H, d, J=4 Hz), 7.74 (1H, s).

| Micro analysis for compound 14: | C | H | S |
| --- | --- | --- | --- |
| Calc'd: | 68.78 | 5.77 | 10.20 |
| Found: | 68.83 | 5.88 | 10.27 |

EXAMPLE 15

Ethyl 3-Methyl-4-hydroxy-5-tert-butyl-7-benzoylbenzofuran-2-carboxylate (15)

To a solution of ethyl 3-methyl-4-hydroxy-5-tert-butylbenzofuran-2-carboxylate, compound 12a (1.00 g, 3.62 mmol) and benzoyl chloride (0.763 g, 5.43 mmol) in 1,2-dichloroethane (40 mL) at 0° C. was added aluminum chloride (0.720 g, 5.43 mmol) and the resulting mixture warmed to reflux for 3.5 hours. The reaction was allowed to cool, poured into 2N HCl (100 mL) and extracted with methylene chloride (4×25 mL). The combined extracts were washed with 5% $NaHCO_3$ (25 mL), dried ($Na_2SO_4$), and concentrated. Flash chromatography using 25% ethyl acetate in hexane as eluant afforded ethyl 3-methyl-4-hydroxy-5-tert-butyl-7-benzoylbenzofuran-2-carboxylate, compound 15 as an oil sufficiently pure for further chemistry. $^1$H NMR d 1.34 (3H, t, J=6 Hz), 1.51 (9H, s), 2.89 (3H, s), 4.35 (2H, q, J=6 Hz), 7.56 (3H, m), 7.86 (3H, m).

EXAMPLE 16

3-Methyl-4-hydroxy-5-tert-butyl-7-benzoylbenzofuran (16)

Ethyl 3-methyl-4-hydroxy-5-tert-butyl-7-benzoylbenzofuran-2-carboxylate, compound 15 (0.408 g, 1.10 mmol) was suspended in a solution of potassium hydroxide (0.185 g, 3.3 mmol) in water (30 mL) and heated to reflux for one hour. The resulting solution was filtered hot, allowed to cool and acidified with 2N HCl. The product precipitated and 3-methyl-4-hydroxy-5-tert-butylbenzofuran-2-carboxylic acid was collected by filtration and vacuum dried. mp 197°–200° C.; $^1$H NMR (DMSO-$d_6$) d 1.40 (9H, s), 2.76 (3H, s), 7.64 (6H, m).

A mixture of 3-methyl-4-hydroxy-5-t-butyl-7-benzoylbenzofuran-2-carboxylic acid (0.334 g, 0.98 mmol), quinoline (1 mL), and copper powder (0.062 g, 0.98 mmol) was warmed to 195° C. until gas evolution had ceased (about 10 minutes). The reaction mixture was allowed to cool and poured into 2N HCl (40 mL). Ethyl acetate (25 mL) was added and the biphasic mixture was filtered through a pad of celite. The layers were separated and the aqueous layer extracted with ethyl acetate (25 mL). The combined organic extracts were dried ($Na_2SO_4$) and concentrated. Flash chromatography using 10% ethyl acetate in hexane as eluant afforded 3-methyl-4-hydroxy-5-tert-butyl-7-benzoylbenzofuran, compound 16 as a white solid after trituration from hexane. $^1$H NMR d 1.49 (9H, s), 2.51 (3H, d, J=2 Hz), 5.78 (1H, s), 7.31 (1H, s), 7.54 (3H, m), 7.66 (1H, s), 7.85 (2H, m).

| Micro analysis for compound 16: | C | H |
| --- | --- | --- |
| Calc'd: | 77.91 | 6.54 |
| Found: | 77.72 | 6.81 |

EXAMPLE 17

Ethyl 3-Methyl-4-hydroxy-5-tert-butyl-7-p-chlorobenzoyl-benzofuran-2-carboxylate (17)

To a solution of ethyl 3-methyl-4-hydroxy-5-tert-butylbenzofuran-2-carboxylate, compound 12a (1.00 g, 3.62 mmol) and p-chlorobenzoyl chloride (0.793 g, 4.53 mmol) in 1,2-dichloroethane (40 mL) at 0° C. was added aluminum chloride (0.604 g, 4.53 mmol) and the mixture heated to reflux for two hours. Additional portions of 4-chlorobenzoyl chloride (0.475 g, 2.71 mmol) and aluminum chloride (0.362 g, 2.71 mmol) were added and the reflux continued for an additional 1.5 hours. The reaction mixture was poured into 2N HCl (100 mL) and extracted with methylene chloride (4×25 mL). The combined extracts were washed with water (25 mL), dried ($Na_2SO_4$), and concentrated. Flash chromatography using 25% ethyl acetate in hexane as eluant afforded ethyl 3-methyl-4-hydroxy-5-tert-butyl-7-p-chlorobenzoylbenzofuran-2-carboxylate, compound 17 as an oil sufficiently pure for further chemistry. $^1$H NMR d 1.34 (3H, t, J=6 Hz), 1.50 (9H, s), 2.88 (3H, s), 4.54 (2H, q, J=6 Hz), 7.47 (2H, d, J=8 Hz), 7.78 (2H, d, J=8 Hz), 7.87 (1H, s).

EXAMPLE 18

3-Methyl-4-hydroxy-5-tert-butyl-7-p-chlorobenzoyl-benzofuran-2-carboxylic acid (18)

Ethyl 3-methyl-4-hydroxy-5-tert-butyl-7-p-chlorobenzoylbenzofuran-2-carboxylate, compound 17 (0.322 g, 0.79 mmol) was suspended in a solution of potassium hydroxide (0.151 g, 2.69 mmol) in water (15 mL) and heated to reflux for 2.5 hours. The resulting solution was cooled in an ice bath and acidified with 2N HCl. The product precipitated and 3-methyl-4-hydroxy-5-tert-butyl-7-p-chlorobenoylbenzofuran-2-carboxylic acid, compound 18 was collected by filtration and allowed to air dry. mp 214°–216° C.; $^1$H NMR (DMSO-$d_6$) d 1.44 (9H, s), 2.78 (3H, s), 5.78 (1H, s), 7.6 (2H, d, J=8 Hz), 7.62 (1H, s), 7.74 (2H, d, J=8 Hz).

EXAMPLE 19

3-Methyl-4-hydroxy-5-tert-butyl-7-p-chlorobenzoyl-benzofuran (19)

A mixture of 3-methyl-4-hydroxy-5-tert-butylbenzofuran-7-p-chlorobenzoylbenzofuran-2-carboxylic acid, compound 18 (0.281 g, 0.73 mmol), copper (0.046 g, 0.73 mmol), and quinoline (1 mL) was heated to 160° C. until gas evolution had ceased. The reaction mixture was allowed to cool and poured into 2N HCl (25 mL). Ethyl acetate (25 mL) was added and the mixture was filtered through a pad of celite. The layers were separated and the aqueous layer reextracted with ethyl acetate (2×20 mL). The combined organic extracts were dried ($Na_2SO_4$) and concentrated. Flash chromatography using 10% ethyl acetate as eluant afforded 3-methyl-4-hydroxy-5-tert-butyl-7-p-chlorobenzoylbenzofuran, compound 19 as an oil which solidified on standing. $^1$H NMR d 1.50 (9H, s), 2.50 (3H, d, J=2 Hz), 5.79 (1H, s), 7.30 (1H, s), 7.46 (2H, d, J=8 Hz), 7.66 (1H, s), 7.79 (2H, d, J=8 Hz).

What is claimed is:

1. A compound of formula (I)

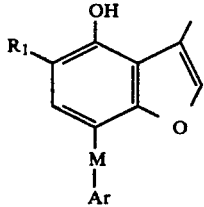

or a pharmaceutically acceptable salt thereof wherein:
$R_1$ is selected from the group consisting of:
(a) hydrogen,
(b) $C_{1-6}$alkyl, and
(c) $C_{3-6}$alkenyl; and M is
(a) a carbon-carbon bond,
(b) —C(H)═C(H)—,
(c) —CH₂C(H)═C(H)—, or

when
Ar is
(a) thienyl,
(b) halotheinyl,
(c) phenyl,
(d) halophenyl,
(e) benzyl,
(f) halobenzyl,
(g) n-methoxypyrrolidinoyl,
(h) γ-lactonyl, or
(i) pyridyl; and
M is —C(H)═, when
Ar is
(j) butyryl lactone, or
(k) cyclopentanone.

2. A compound according to claim 1 wherein
M is
(a) a carbon-carbon bond,
(b) —C(H)═C(H)—, or

Ar is
(a) thienyl,
(b) halothienyl,
(c) phenyl, or
(d) halophenyl.

3. A compound according to claim 2 wherein:
$R_1$ is
(a) hydrogen,
(b) alkyl,
(c) n-propyl, or
(d) tert-butyl; and
Ar is
(a) thienyl,
(b) chlorothienyl,
(c) phenyl, or
(d) chlorophenyl.

4. A compound according to claim 3 selected from the group consisting of:
(1) 7-(2-thienoyl)-4-hydroxy-3-methylbenzofuran,
(2) 7-benzoyl-4-hydroxy-3-methylbenzofuran,
(3) 7-(2-thienoyl)-5-allyl-4-hydroxy-3-methylbenzofuran,
(4) 7-(2-thienoyl)-5-(n-propyl)-4-hydroxy-3-methylbenzofuran,
(5) 7-(2-thienoyl)-5-tert-butyl-4-hydroxy-3-methylbenzofuran,
(6) 7-benzoyl-5-tert-butyl-4-hydroxy-3-methylbenzofuran, and
(7) 7-(p-Cl-benzoyl)-5-tert-butyl-4-hydroxy-3-methylbenzofuran,
or a pharmaceutically acceptable salt thereof.

5. A pharmaceutical composition for treating leukotriene mediated diseases comprising a pharmaceutical carrier and a non-toxic effective amount of a compound according to claim 1.

6. A pharmaceutical composition according to claim 5 wherein the compound is selected from the group consisting of:
(a) 7-(2-thienoyl)-4-hydroxy-3-methylbenzofuran,
(b) 7-benzoyl-4-hydroxy-3-methylbenzofuran,
(c) 7-(2-thienoyl)-5-allyl-4-hydroxy-3-methylbenzofuran,
(d) 7-(2-thienoyl)-5-(n-propyl)-4-hydroxy-3-methylbenzofuran,
(e) 7-(2-thienoyl)-5-tert-butyl-4-hydroxy-3-methylbenzofuran,
(f) 7-benzoyl-5-tert-butyl-4-hydroxy-3-methylbenzofuran, and
(g) 7-(p-Cl-benzoyl)-5-tert-butyl-4-hydroxy-3-methylbenzofuran,
or a pharmaceutically acceptable salt thereof.

7. A method of treating leukotriene mediated diseases comprising the administration to a subject in need of such treatment a therapeutically effective amount of a compound according to claim 1.

8. A method of treating inflammation according to claim 7 wherein the compound is selected from the group consisting of:
(a) 7-(2-thienoyl)-4-hydroxy-3-methylbenzofuran,
(b) 7-benzoyl-4-hydroxy-3-methylbenzofuran,
(c) 7-(2-thienoyl)-5-allyl-4-hydroxy-3-methylbenzofuran,
(d) 7-(2-thienoyl)-5-(n-propyl)-4-hydroxy-3-methylbenzofuran,
(e) 7-(2-thienoyl)-5-tert-butyl-4-hydroxy-3-methylbenzofuran,
(f) 7-benzoyl-5-tert-butyl-4-hydroxy-3-methylbenzofuran, and
(g) 7-(p-Cl-benzoyl)-5-tert-butyl-4-hydroxy-3-methylbenzofuran,
or a pharmaceutically acceptable salt thereof.

* * * * *